United States Patent [19]

Sucrow et al.

[11] Patent Number: 4,663,073

[45] Date of Patent: May 5, 1987

[54] TERCYCLOHEXYLS

[75] Inventors: Wolfgang Sucrow, Paderborn; Herbert Wolter, Paderborn-Barkhausen; Rudolf Eidenschink, Münster, all of Fed. Rep. of Germany

[73] Assignee: Merck Patent Gesellschaft mit beschrankter Haftung, Darmstadt, Fed. Rep. of Germany

[21] Appl. No.: 754,307

[22] Filed: Jul. 12, 1985

[30] Foreign Application Priority Data

Jul. 14, 1984 [DE] Fed. Rep. of Germany ....... 3426035
Jul. 18, 1984 [DE] Fed. Rep. of Germany ....... 3426522

[51] Int. Cl.[4] .................. C07C 43/84; C07C 121/46; C07C 69/75; C07C 69/757; C07C 49/313; C07C 49/35; C07C 43/115; C09K 19/30; G02F 1/13
[52] U.S. Cl. ................. 252/299.63; 252/299.5; 350/350 R; 558/431; 560/1; 560/116; 560/117; 560/231; 568/367; 568/664
[58] Field of Search .......... 252/299.63, 299.5; 350/350 R; 260/464; 560/116, 1, 117, 141, 231; 568/367, 664; 558/431

[56] References Cited

U.S. PATENT DOCUMENTS

| 4,229,315 | 10/1980 | Krause et al. ................. 252/299.63 |
| 4,331,552 | 5/1982 | Eidenschink et al. ......... 252/299.63 |
| 4,335,011 | 6/1982 | Sethofer ........................ 252/299.61 |
| 4,405,488 | 9/1983 | Sugimori et al. ............... 252/299.6 |
| 4,419,263 | 12/1983 | Praeflke et al. ............... 252/299.63 |
| 4,422,951 | 12/1983 | Sugimori et al. ............. 252/299.63 |
| 4,432,885 | 2/1984 | Petrzilka et al. ............. 252/299.62 |
| 4,434,073 | 2/1984 | Sucrow et al. ................ 252/299.62 |
| 4,439,340 | 2/1984 | Kojima et al. ................ 252/299.63 |
| 4,477,369 | 10/1984 | Sugimori et al. ............... 252/299.5 |
| 4,502,974 | 3/1985 | Sugimori et al. ............... 252/299.5 |
| 4,507,222 | 2/1985 | Inoue et al. .................. 252/299.63 |
| 4,510,069 | 4/1985 | Eidenschink et al. ......... 252/299.63 |
| 4,534,883 | 8/1985 | Sugimori et al. ............. 252/299.63 |
| 4,564,694 | 1/1986 | Hirai et al. ................... 252/299.67 |
| 4,572,794 | 2/1986 | Eidenschink et al. ......... 252/299.63 |

FOREIGN PATENT DOCUMENTS

| 87032 | 8/1983 | European Pat. Off. ....... 252/299.63 |
| 3211601 | 10/1983 | Fed. Rep. of Germany ................. 252/299.63 |
| 57-171936 | 10/1982 | Japan ............................ 252/299.63 |
| 59-141540 | 8/1984 | Japan ............................ 252/299.63 |
| 59-157056 | 9/1984 | Japan ............................ 252/299.63 |
| 85/01295 | 3/1985 | PCT Int'l Appl. ............ 252/299.63 |
| 2092169 | 8/1982 | United Kingdom ........... 252/299.63 |

OTHER PUBLICATIONS

Billard, J., et al, Mol. Cryst. Liq. Cryst., vol. 41 (Letters), pp. 217–222 (1978).

Demus, D., et al., Flüssige Kristacle in Tabellen, VEB Deutscher Verlag für Grundstoffindustrie, Leipzig, p. 34 (1974).

Primary Examiner—Teddy S. Gron
Attorney, Agent, or Firm—Millen & White

[57] ABSTRACT

Liquid-crystalline tercyclohexyls of the formula

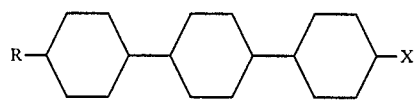

in which

R is an alkyl group with 1–12 C atoms, in which one or two non-adjacent $CH_2$ groups can be replaced by 0, X is —CN, —COOR$^1$, —OOCR$^1$, —COR$^1$ or R$^1$, and R$^1$ is an alkyl group having 1–12 C atoms, with the proviso that in the case where X=R$^1$ at least one $CH_2$ group in the alkyl group R is replaced by 0, and useful in liquid-crystalline dielectrics.

10 Claims, No Drawings

TERCYCLOHEXYLS

The invention relates to new tercyclohexyls.

SUMMARY OF THE INVENTION

It is an object of this invention to provide new, stable liquid-crystalline or mesogenic compounds which are suitable as components in liquid-crystalline dielectrics.

Upon further study of the specification and appended claims, further objects and advantages of this invention will become apparent to those skilled in the art.

These objects have been achieved by providing components of the formula I

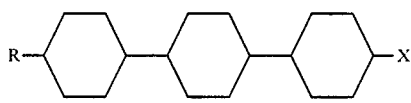

in which

R is an alkyl group having 1–12 C atoms, in which one or two non-adjacent $CH_2$ groups can be replaced by O, X is —CN, —$COOR^1$, —$OOCR^1$, —$COR^1$ or $R^1$, and $R^1$ is an alkyl group having 1–12 C atoms, with the proviso that in the case where $X=R^1$ at least one $CH_2$ group in the alkyl group R is replaced by O.

The compounds of the formula I can be used as similar compounds, for example those known from German Offenlegungsschrift No. 2,702,598, as components in liquid-crystalline dielectrics, in particular for displays based on the principle of the twisted cell, the guest-host effect, the effect of deformation of aligned phases, or the effect of dynamic scattering.

DETAILED DISCUSSION

It has been found that the compounds of the formula I are excellently suitable as components of liquid-crystalline dielectrics. In particular, it is possible with their aid to prepare stable liquid-crystalline phases which have relatively low optical anisotropy and pronounced nematic characteristics and which are distinguished in electrooptical display elements based on the principle of the twisted cell and/or the guest-host effect by a particularly favourable angular dependence of the contrast.

In addition, by making available the compounds of the formula I, there has been, quite generally, a considerable extension in the range of liquid-crystalline substances which are suitable from various viewpoints of applications technology for the preparation of nematic mixtures.

The compounds of the formula I have a wide range of applications. Depending on the choice of the substituents, these compounds can be used as basic materials from which liquid-crystalline phases are predominantly composed, but it is also possible to add to compounds of the formula I liquid-crystalline basic materials of other classes of compounds, in order, for example, to affect the angular dependence of the contrast and/or the optical anisotropy of a phase of this type. The compounds of the formula I are also suitable as intermediates for the preparation of other substances which can be used as constituents of liquid-crystalline dielectrics.

The compounds of the formula I are, in the pure state, colorless and form liquid-crystalline mesophases in a temperature range which is favorable for electrooptical use. They are very stable to chemicals, heat and light.

Thus the invention relates to the compounds of the formula I and to a process for their preparation, which is characterised in that for the preparation of carbonitriles of the formula I (X=CN) the corresponding tercyclohexylcarboxylic acids (X=COOH), or one of their reactive derivatives, are converted into the corresponding amides, and the latter are dehydrated, or an appropriate acid chloride is reacted with sulfamide, or in that for the preparation of carboxylic esters of the formula I (X=—$COOR_1$) the corresponding carboxylic acid compounds, or one of their reactive derivatives, are reacted with an appropriate alcohol or one of its reactive derivatives, or in that for the preparation of acyl compounds of the formula I (X=—$COR^1$) the corresponding carboxylic acid compounds, or one of their reactive derivatives, are converted into the corresponding nitriles, and the latter are reacted with an appropriate Grignard compound, or in that for the preparation of the alkoxy/alkyl compounds (X=$R^1$) the corresponding carboxylic acid compounds, or one of their reactive derivatives, are converted into the corresponding keto compounds (X=$COR^1$) and the latter are reduced, or in that a compound which corresponds to formula I apart form containing, in place of H atoms, one or more reducible groups and/or C—C bonds, is treated with a reducing agent, or in that for the preparation of tercyclohexyls of the formula I'

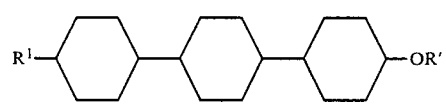

in which

R' is an alkyl group having 1–11 C atoms, in which one additional $CH_2$ group non-adjacent to O can be replaced by O, and $R^1$ is an alkyl group having 1–12 C atoms, characterised in that the corresponding tercyclohexanols (R'=H), or one of their reactive derivatives, are etherified, or in that for the preparation of alkanoyloxy derivatives of the formula I (X=—$OOCR^1$) the corresponding tercyclohexanols (X=OH), or one of their reactive derivatives, are reacted with an appropriate carboxylic acid or one of its reactive derivatives.

The invention also relates to the use of the compounds of the formula I as components of liquid-crystalline phases. Furthermore, the invention relates to liquid-crystalline phases containing at least one compound of the formula I and to liquid-crystal display elements, in particular electrooptical display elements, which contain phases of this type.

For reasons of simplicity, in the following text "Cyc" means 1,4-cyclohexylene group.

The stereoisomers of the compounds of the formula I which are preferred are those in which all three 1,4-cyclohexylene groups are substituted trans in the 1,4-position.

Accordingly, the compounds of the formula I preferably comprise compounds of the part formula Ia to If

| | |
|---|---|
| R-Cyc-Cyc-Cyc-CN | Ia |
| R-Cyc-Cyc-Cyc-$R^1$ | Ib |

R-Cyc-Cyc-Cyc-COOR¹             Ic

R-Cyc-Cyc-Cyc-CO-R¹             Id

R-Cyc-Cyc-Cyc-OOCR¹             Ie

R¹-Cyc-Cyc-Cyc-CH₂OAlkyl           If

Compounds of the part formulae Ia-Ic and Ie, in particular Ia, Ib and Ie, are preferably used. Ib and Ie are particularly preferred.

Also preferred are the compounds of the part formulae Ia and Ic with an axial —CN or —COOR¹ group, that is to say the compounds of the part formulae Iaa and Ica:

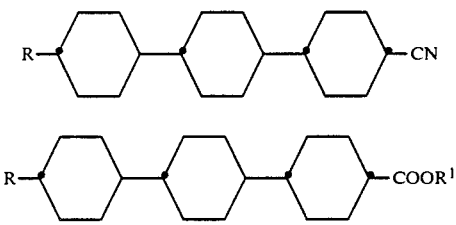

In the compounds of the formulae given above and below, it is possible for the alkyl radicals R, in which it is also possible for one ("alkoxy" or "oxaalkyl") or two ("alkoxyalkoxy" or "dioxaalkyl") non-adjacent CH₂ groups to be replaced by 0 atoms, to be straight-chain or branched. They are preferably straight-chain and have 2, 3, 4, 5, 6, 7, 8, 9 or 10 C atoms, and are accordingly ethyl, propyl, butyl, pentyl, hexyl, heptyl, octyl, nonyl, decyl, ethoxy, propoxy, butoxy, pentoxy, hexoxy, heptoxy, octoxy, nonoxy, decoxy, 2-oxapropyl (=methoxymethyl), 2(=ethoxymethyl) or 3-oxabutyl (=2-methoxymethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, also methyl, undecyl, dodecyl, methoxy, undecoxy, dodecoxy, 2-, 3-, 4-, 5-, 6-, 7-, 8-, 9- or 10-oxaundecyl, 2-, 3-, 4-, 5-, 6-, 7-, 8-, 9-, 10- or 11-oxadodecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, 1,3-, 1,4-, 1,5-, 1,6-, 2,4-, 2,5-, 2,6-, 3,5-, 3,6- or 4,6-dioxaheptyl, 1,3-, 1,4-, 1,5-, 1,6-, 1,7-, 2,4-, 2,5-, 2,6-, 2,7-, 3,5-, 3,6-, 3,7-, 4,6-, 4,7- or 5,7-dioxaoctyl, 1,3-, 1,4-, 1,5-, 1,6-, 1,7-, 1,8-, 2,4-, 2,5-, 2,6-, 2,7-, 2,8-, 3,5-, 3,6-, 3,7-, 3,8-, 4,6-, 4,7-, 4,8-, 5,7- or 5,8-dioxanonyl, 1,3-, 1,4-, 1,5-, 1,6-, 1,7-, 1,8-, 1,9-, 2,4-, 2,5-, 2,6-, 2,7-, 2,8-, 2,9-, 3,5-, 3,6-, 3,7-, 3,8-, 3,9-, 4,6-, 4,7-, 4,8-, 4,9-, 5,7-, 5,8- or 5,9-dioxadecyl.

In the case where X=—CN, —COOR¹, OOCR¹ or —COR¹, R is preferably alkyl or alkoxy, in particular n-alkyl; in the case where X=R¹ it is preferably n-alkoxy or n-oxaalkyl, and is particularly preferably n-alkoxy.

Compounds of the formulae I and Ia to If having branched wing groups R or R¹ can occasionally be of significance, because of improved solubility in the customary liquid-crystalline basic materials, but are of particular importance as chiral doping agents when they are optically active. Branched groups of this type contain, as a rule, not more than one chain branch. Preferred branched radicals R and R¹ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl and 3-oxa-4-methylpentyl. Compounds of this type are suitable as components of ferroelectric liquid-crystal phases.

Those compounds of the formulae I and Ia to If which are preferred are those in which at least one of the radicals contained therein has one of the preferred meanings indicated.

Particularly preferred groups of compounds correspond to the formulae Ig to Il:

Alkyl-Cyc-Cyc-Cyc-CN            Ig

Alkoxy-Cyc-Cyc-Cyc-CN          Ih

Alkoxy-Cyc-Cyc-Cyc-alkyl         Ii

Alkyl-Cyc-Cyc-Cyc-COOAlkyl      Ij

Alkyl-Cyc-Cyc-Cyc-OOCAlkyl      Ik

Alkyl-Cyc-Cyc-Cyc-CH₂OAlkyl     Il in which the alkyl and alkoxy groups have 1-10, preferably 2-8, C atoms, are preferably straight-chain, and it being possible for the two alkyl groups in Ij, Ik, and Il to be identical to or different from one another.

Additional preferred compounds of the formula I correspond to the formulae Im to Io:

n-alkyl-Cyc-Cyc-Cyc-OOC-CH₂CH₂CH₃    Im n-alkyl-Cyc-Cyc-Cyc-O-CH₂CH₃         In n-alkyl-Cyc-Cyc-Cyc-O-CH₂CH₂CH₂CH₃   Io in which the n-alkyl groups have 2-8 C atoms.

The compounds of the formula I can be prepared by methods which are known per se and are described in the literature (for example in the standard works, such as Houben-Weyl, Methoden der Organischen Chemie (Methods of organic chemistry), published by Georg-Thieme, Stuttgart), in particular under reaction conditions which are known and suitable for the reactions mentioned. It is also possible to make use for this of variants which are not mentioned here in detail but are known per se.

The starting materials can also, if desired, be formed in situ, in such a manner that they are not isolated from the reaction mixture but are immediately reacted further to give the compounds of formula I. The starting materials which are preferably used are the corresponding bicyclohexylcyclohexanecarboxylic acids, whose preparation has been described in European Patent No. 90671 as intermediates, which were not characterised in detail, in the synthesis of liquid-crystalline 4-ring systems.

Apart from the appropriate free tercyclohexylcarboxylic acids, their reactive derivatives are also suitable.

Particularly suitable reactive derivatives of the carboxylic acids mentioned are the acid halides, particularly the chlorides and bromides, also the anhydrides, azides or esters, in particular alkyl esters having 1–4 C atoms in the alkyl group.

Furthermore, preferred starting materials which are used are the corresponding bicyclohexylcyclohexanols, whose preparation has been described in European Patent No. 90671 as intermediates, which were not characterised in detail, in the synthesis of liquid-crystalline 4-ring systems.

Apart from the appropriate free tercyclohexanols, their reactive derivatives are also suitable.

Suitable reactive derivatives of the alcohols mentioned are, in particular, the corresponding metal alcoholates of the formula $R^1OM$, in which M is one equivalent of a metal, preferably an alkali metal, such as Na or K.

It is possible for the preparation of the nitriles of the formula I ($X=CN$) to dehydrate corresponding amides in which a $CONH_2$ group is in place of a CN group. The amides can be obtained from, for example, the corresponding acid halides by reaction with ammonia. The corresponding acid halides can in turn be prepared in a known manner from the corresponding carboxylic acids, for example using thionyl chloride. Examples of suitable water-eliminating agents for the dehydration of the amides are inorganic acid chlorides, such as $SOCl_2$, $PCl_3$, $PCl_5$, $POCl_3$, $SO_2Cl_2$ and $COCl_2$, as well as $P_2O_5$, $AlCl_3$ (for example as a double compound with NaCl), aromatic sulfonic acids and sulfonyl halides. This reaction can be carried out in the presence or absence of an inert solvent, at temperatures between about 0° and 150°; examples of suitable solvents are bases, such as pyridine or triethylmine, aromatic hydrocarbons, such as benzene, toluene or xylene, or amides, such as DMF.

It is also possible for the preparation of the nitriles of the formula I to react appropriate acid halides, preferably the chlorides, with sulfamide, preferably in an inert solvent such as tetramethylene sulfone, at temperatures between about 80° and 150°, preferably at 120°. The nitriles can be isolated directly after the customary work-up.

For the preparation of the esters of the formula I ($X=-OOCR^1$), preferably an appropriate tercyclohexanol, or one of its reactive derivatives, is reacted with an appropriate carboxylic acid or one of its reactive derivatives.

For the preparation of the esters of the formula I ($X=-COOR^1$), preferably an appropriate carboxylic acid, or one of its reactive derivatives, is reacted with an appropriate alcohol or one of its reactive derivatives.

Particularly suitable reactive derivatives of the alcohols mentioned are the corresponding metal alcoholates of the formula $R^1OM$, in which M is one equivalent of a metal, preferably an alkali metal, such as Na or K.

Particularly suitable reactive derivatives of the carboxylic acids mentioned are the acid halides, in particular the chlorides and bromides, also the anhydrides, azides or esters, in particular alkyl esters having 1–4 C atoms in the alkyl group.

The esterification is advantageously carried out in the presence of an inert solvent. Particularly well suited are ethers, such as diethyl ether, di-n-butyl ether, THF, dioxane or anisole, ketones, such as acetone, butanone or cyclohexanone, amides, such as DMF or phosphoric hexamethyltriamide, hydrocarbons, such as benzene, toluene or xylene, halogenated hydrocarbons, such as carbon tetrachloride or tetrachloroethylene, and sulfoxides, such as dimethyl sulfoxide or sulfolane. Solvents which are immiscible with water can at the same time advantageously be used for the removal by azeotropic distillation of the water formed in the esterification. Occasionally, it is also possible for an excess of an organic base, for example pyridine, quinoline or triethylamine, to be used for the solvent for the esterification. The esterification can also be carried out in the absence of a solvent, for example by simply heating the components in the presence of sodium acetate. The reaction temperature is usually between −50° and +250°, preferably between −20° and +80°. At these temperatures, the esterification reactions are, as a rule, complete after 15 minutes to 48 hours.

The specific reaction conditions for the esterification substantially depend on the nature of the starting materials used. Thus, as a rule, a free carboxylic acid is reacted with a free alcohol in the presence of a strong acid, for example a mineral acid, such as hydrochloric acid or sulfonic acid. A preferred reaction procedure is the reaction of an acid anhydride or, in particular, an acid chloride with an alcohol, preferably in a basic medium, particularly important bases being alkali metal carbonates and bicarbonates, such as sodium carbonate, sodium bicarbonate, potassium carbonate or potassium bicarbonate, alkali metal acetates, such as sodium or potassium acetate, alkaline earth metal hydroxides, such as calcium hydroxide, or organic bases, such as triethylamine, pyridine, lutidine, collidine or quinoline. Another preferred embodiment of the esterification comprises intitial conversion of the alcohol into the sodium or potassium alcoholate, for example by treatment with ethanolic sodium or potassium hydroxide solution, isolation of the latter and suspension thereof, with stirring, in acetone or diethyl ether together with sodium bicarbonate or potassium carbonate, and addition to this suspension of a solution of the acid chloride or an anhydride in diethyl ether, acetone or DMF, advantageously at temperatures between about −25° and +20°.

For the prparation of the acyl compounds of the formula I ($X=-CO-R^1$) from the corresponding carboxylic acids, first the corresponding nitrile is prepared as described. The latter is preferably reacted in a manner known per se with a Grignard compound of the general formula $R^1MHal$, in which M is a metal, preferably magnesium, and Hal is a halogen, preferably bromide, and then hydrolysis is carried out. The Grignard compound is prepared in a known manner with magnesium and the appropriate alkyl halide $R^1Hal$, preferably $R^1Br$, in an ether, preferably diethyl ether or tetrahydrofuran, under conditions customary for reactions of this type.

For the preparation of the alkoxy-alkyl compounds of the formula I ($X=R^1$), preferably the corresponding ketones ($X=-CO-R^1$) are reduced to the corresponding compounds of the formula I by the methods of Clemmensen (with zinc, amalgamated zinc or tin and hydrochloric acid, preferably in an aqueous alcoholic solution or in a heterogeneous phase with water/toluene, at temperatures between about 80° and 120°) or Wolff-Kishner (with hydrazine, preferably in the presence of alkali, such as KOH or NaOH, in a high-boiling solvent, such as diethylene glycol or triethylene glycol, at temperatures between about 100° and 200°).

The compounds of the formula I can also be prepared by reduction of compounds which correspond to the formula I apart from containing, in place of H atoms, one or more reducible groups and/or C—C bonds.

Suitable and preferred reducible groups are carbonyl groups, in particular keto groups, also, for example, free or esterified hydroxyl groups. Preferred starting materials for the reduction correspond to the formula I, but can contain a cyclohexene ring or a cyclohexanone ring in place of a cyclohexane ring, and/or a —CO-group in place of a —CH$_2$CH$_2$-group, and/or a —CO-group in place of a CH$_2$-group, and/or a free or a functionally modified (for example in the form of its p-toluenesulfonate) OH group in place of a H atom.

The reduction can be carried out by, for example, catalytic hydrogenation at tempertures between about 0° and about 200°, and under pressures between about 1 and 200 bar, in an inert solvent, for example an alcohol, such as methanol, ethanol or isopropanol, an ether, such as tetrhydrofuran (THF) or dioxane, an ester such as ethyl acetate, a carboxylic acid such as acetic acid, or a hydrocarbon such as cyclohexane. Suitable and preferred catalysts are noble metals such as Pt or Pd, which can be used in the form of oxides (for example PtO$_2$ or PdO), on a support (for example Pd on charcoal, calcium carbonate or strontium carbonate) or in a finely divided form.

For the preparation of the ethers of the fomula I', preferably an appropriate tercyclohexanol, or one of its reactive derivatives, is reacted with an appropriate alkyl halide, sulfonate or dialkyl sulfate, preferably in an inert solvent, such as acetone, 1,2-dimethoxyethane, DMF or dimethyl sulfoxide, or an excess of aqueous or aqueous-alcoholic NaOH or KOH, at temperatures between about 20° and 100°.

The hydroxyl compound is preferably converted into an appropriate metal derivative beforehand, for example by treatment with NaH, NaNH$_2$, NaOH, KOH, Na$_2$CO$_3$ or K$_2$CO$_3$ into the corresponding alkali metal alcoholate.

The dielectrics according to the invention comprise 2 to 25, preferably 3 to 15, components, including at least one compound of the formula I. The other constituents are preferably selected from the nematic or nematogenic substances, in particular the known substances from the classes of azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-biscyclohexylbenzenes, 4,4'-biscyclohexylbiphenyls, phenylpyrimidines or cyclohexylpyrimidines, phenyldioxanes or cyclohexyldioxanes, 1,2-biscyclohexylethanes, 1-cyclohexyl-2-phenylethanes, 1,2-benzyl phenyl ethers, tolanes and substituted cinnamic acids.

The most important compounds which are suitable as constituents of liquid-crystalline dielectrics of this type my be characterised by the formula II.

R'-L-G-E-R''    II in which L and E is each a carbocyclic or heterocyclic ring system from the group formed by 1,4-phenylene and trans-1,4-cyclohexyl rings, and 4,4'-disubstituted biphenyl, phenylcyclohexane and cyclohexylcyclohexane systems, 2,5-disubstituted pyrimidine and 1,3-dioxane rings, 2,6-disubstituted naphthalene, dihydronaphthalene and tetrahydronaphthalene, quinazoline and tetrahydroquinazoline, which are unsubstituted or substituted by one or two F and/or Cl atoms and/or CH$_3$ groups and/or CN groups,

| —CH=CH— | —N(O)=N— |
| —CH=CY— | —CH=N(O)— |
| —C≡C— | —CH$_2$—CH$_2$— |
| —CO—O— | —CH$_2$—O— |
| —CO—S— | —CH$_2$—S— |

-continued

| —CH=N— | —COO—Phe—COO— | or a C—C single bond, Y is halogen, preferably chlorine, or —CN, and R' and R'' are alkyl, alkoxy, alkanoyloxy or alkoxycarbonyloxy having up to 18, preferably up to 8, carbon atoms, or one of these radicals is CN, NC, NO$_2$, CF$_3$, F, Cl or Br.

In most of these compounds, R' and R'' differ from one another, one of these radicals usually being an alkyl or alkoxy group. However, other variants of the envisaged substituents can also be used. Many substances of these types and mixtures thereof are obtainable commercially. All these substances can be prepared by methods known from the literature.

The dielectrics according to the invention contain, as a rule, at least 30, preferably 50–99, in particular 60–98, % by weight of the compounds of the formulae I and II. Of these, preferably at least 5% by weight, and usually 10–40% by weight, is of one or more compounds of the formula I. However, the invention also comprises those liquid-crystalline dielectrics to which, for example for doping purposes, only less than 5% by weight, for example 0.1 to 3% by weight, of one or more compounds of the formula I have been added. On the other hand, compounds of the formula I can contribute up to 60% by weight of the dielectrics according to the invention. The liquid-crystalline dielectrics according to the invention preferably contain 10 to 30% by weight of one or more compounds of the formula I.

The dielectrics according to the invention are prepared in a manner customary per se. As a rule, the components are dissolved in one another, preferably at elevated temperature. The liquid-crystalline dielectrics according to the invention can be modified by suitable additives in such a manner that they can be used in all types of liquid-crystal display elements which have been disclosed hitherto.

Additives of these types are known to the expert and are described in detail in the literature. For example, it is possible to add conducting salts, preferably ethyldimethyldodecylammonium 4-hexyloxybenzoate, tetrabutylammonium tetraphenylboronate or complex salts of crown ethers (see, for example, I. Haller et al., Mol. Cryst. Liq. Cryst. Volume 24, pages 249–258 (1973)) to improve the conductivity, dichroic dyes to prepare coloured guest-host systems, or substances to modify the dielectric anisotropy, the viscosity and/or the orientation of the nematic phases. Substances of these types are described in, for example, German Offenlegungsschriften Nos. 2,209,127, 2,240,864, 2,321,632, 2,338,281, 2,450,088, 2,637,480, 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples and in the preceding text, all temperatures are set forth uncorrected in degrees Celsius and all parts and percentages are by weight, unless otherwise indicated.

In the examples, m.p. is the melting point and c.p. is the clear point of a liquid crystal substance.

EXAMPLES 1-18

Example 1

(a) 36 g of 4-bicyclohexylylcyclohexylcarboxylic acid are heated together with 50 g of thionyl chloride to reflux for 16 h. After removal of the excess thionyl chloride by distillation, the residue remaining is 36.8 g of crude trans,trans-4-(trans-4-propylbicyclohexyl)-cyclohexanecarbonyl chloride.

(b) 17 g of the acid chloride are dissolved in 100 ml of 1,4-dioxane, and this solution is added to 200 ml of a 10% aqueous ammonia solution at room temperature. The precipitated carboxamide is filtered off with suction and, after drying, is recrystallized from a mixture of equal parts by volume of dioxane and ethanol. Yield: 12.3 g of trans,trans-4-(trans-4-propylbicyclohexyl)cyclohexanecarboxamide.

(c) 12 g of amine are suspended in 150 ml of N,N-dimethylformamide. 25 g of phosphorus oxytrichloride are added to the suspension at 40° C., during which the temperature of the mixture should not exceed 50° C. Thereafter, it is stirred at 45° C. for 3 h and then poured into 1,000 ml of ice-water. The mixture is extracted 3 times with 100 ml of dichloromethane, and the combined organic phases are washed with water. The residue remaining after drying with sodium sulfate and removal of the solvent by distillation is recrystallised from ethanol. Yield: 7.9 g of trans,trans-4-(trans-4-propylbicyclohexyl)cyclohexanecarbonitrile, m.p. 95° C., c.p. 236° C.

The following are prepared analogously:

2. trans,trans-4-(trans-4-ethylbicyclohexyl)cyclohexane-1-carbonitrile
3. trans,trans-4-(trans-4-butylbicyclohexyl)cyclohexane-1-carbonitrile
4. trans,trans-4-(trans-4-pentylbicyclohexyl)cyclohexane-1-carbonitrile
5. trans,trans-4-(trans-4-hexylbicyclohexyl)cyclohexane-1-carbonitrile
6. trans,trans-4-(trans-4-heptylbicyclohexyl)cyclohexane-1-carbonitrile
7. trans,trans-4-(trans-4-octylbicyclohexyl)cyclohexane-1-carbonitrile
8. trans,trans-4-(trans-4-nonylbicyclohexyl)cyclohexane-1-carbonitrile
9. trans,trans-4-(trans-4-decylbicyclohexyl)cyclohexane-1-carbonitrile
10. trans,trans-4-(trans-4-ethoxybicyclohexyl)cyclohexane-1-carbonitrile
11. trans,trans-4-(trans-4-propoxybicyclohexyl)cyclohexane-1-carbonitrile
12. trans,trans-4-(trans-4-butoxybicyclohexyl)cyclohexane-1-carbonitrile
13. trans,trans-4-(trans-4-pentoxybicyclohexyl)cyclohexane-1-carbonitrile
14. trans,trans-4-(trans-4-hexoxybicyclohexyl)cyclohexane-1-carbonitrile
15. trans,trans-4-(trans-4-heptoxybicyclohexyl)cyclohexane-1-carbonitrile
16. trans,trans-4-(trans-4-octoxybicyclohexyl)cyclohexane-1-carbonitrile
17. trans,trans-4-(trans-4-nonoxybicyclohexyl)cyclohexane-1-carbonitrile
18. trans,trans-4-(trans-4-decoxybicyclohexyl)cyclohexane-1-carbonitrile

EXAMPLES 19-108

Example 19

17 g of the acid chloride obtained in Example 1 are dissolved in 100 ml of methanol, and 2.5 ml of pyridine are added to the solution at room temperature. After stirring at room temperature for 3 hours, the excess methanol is substantially removed by distillation, and 200 ml of water are added to the residue remaining. The resulting emulsion is extracted several times with 100 ml of dichloromethane each time. 13.2 g of methyl trans,trans-4(trans-4-propylbicyclohexyl)cyclohexanecarboxylate are obtained from the organic phase after recrystallization from methanol, m.p. 69° C., c.p. 240° C.

The following are prepared analogously:

20. ethyl trans,trans-4-(trans-4-propylbicyclohexyl)cyclohexanecarboxylate
21. propyl trans,trans-4-(trans-4-propylbicyclohexyl)cyclohexanecarboxylate
22. butyl trans,trans-4-(trans-4-propylbicyclohexyl)cyclohexanecarboxylate
23. pentyl trans,trans-4-(trans-4-propylbicyclohexyl)cyclohexanecarboxylate
24. hexyl trans,trans-4-(trans-4-propylbicyclohexyl)cyclohexanecarboxylate
25. heptyl trans,trans-4-(trans-4-propylbicyclohexyl)cyclohexanecarboxylate
26. octyl trans,trans-4-(trans-4-propylbicyclohexyl)cyclohexanecarboxylate
27. nonyl trans,trans-4-(trans-4-propylbicyclohexyl)cyclohexanecarboxylate
28. decyl trans,trans-4-(trans-4-propylbicyclohexyl)cyclohexanecarboxylate
29. methyl trans,trans-4-(trans-4-ethylbicyclohexyl)cyclohexanecarboxylate
30. ethyl trans,trans-4-(trans-4-ethylbicyclohexyl)cyclohexanecarboxylate
31. propyl trans,trans-4-(trans-4-ethylbicyclohexyl)cyclohexanecarboxylate
32. butyl trans,trans-4-(trans-4-ethylbicyclohexyl)cyclohexanecarboxylate
33. pentyl trans,trans-4-(trans-4-ethylbicyclohexyl)cyclohexanecarboxylate
34. hexyl trans,trans-4-(trans-4-ethylbicyclohexyl)cyclohexanecarboxylate
35. heptyl trans,trans-4-(trans-4-ethylbicyclohexyl)cyclohexanecarboxylate
36. octyl trans,trans-4-(trans-4-ethylbicyclohexyl)cyclohexanecarboxylate
37. nonyl trans,trans-4-(trans-4-ethylbicyclohexyl)cyclohexanecarboxylate
38. decyl trans,trans-4-(trans-4-ethylbicyclohexyl)cyclohexanecarboxylate
39. methyl trans,trans-4-(trans-4-butylbicyclohexyl)cyclohexanecarboxylate
40. ethyl trans,trans-4-(trans-4-butylbicyclohexyl)cyclohexanecarboxylate
41. propyl trans,trans-4-(trans-4-butylbicyclohexyl)cyclohexanecarboxylate
42. butyl trans,trans-4-(trans-4-butylbicyclohexyl)cyclohexanecarboxylate
43. pentyl trans,trans-4-(trans-4-butylbicyclohexyl)cyclohexanecarboxylate
44. hexyl trans,trans-4-(trans-4-butylbicyclohexyl)cyclohexanecarboxylate
45. heptyl trans,trans-4-(trans-4-butylbicyclohexyl)cyclohexanecarboxylate 46. octyl trans,trans-4-(trans-4-butylbicyclohexyl)cyclohexanecarboxylate
47. nonyl trans,trans-4-(trans-4-butylbicyclohexyl)cyclohexanecarboxylate
48. decyl trans,trans-4-(trans-4-butylbicyclohexyl)cyclohexanecarboxylate
49. methyl trans,trans-4-(trans-4-pentylbicyclohexyl)cyclohexanecarboxylate
50. ethyl trans,trans-4-(trans-4-pentylbicyclohexyl)cyclohexanecarboxylate
51. propyl trans,trans-4-(trans-4-pentylbicyclohexyl)cyclohexanecarboxylate
52. butyl trans,trans-4-(trans-4-pentylbicyclohexyl)cyclohexanecarboxylate
53. pentyl trans,trans-4-(trans-4-pentylbicyclohexyl)cyclohexanecarboxylate
54. hexyl trans,trans-4-(trans-4-pentylbicyclohexyl)cyclohexanecarboxylate
55. heptyl trans,trans-4-(trans-4-pentylbicyclohexyl)cyclohexanecarboxylate
56. octyl trans,trans-4-(trans-4-pentylbicyclohexyl)cyclohexanecarboxylate
57. nonyl trans,trans-4-(trans-4-pentylbicyclohexyl)cyclohexanecarboxylate
58. decyl trans,trans-4-(trans-4-pentylbicyclohexyl)cyclohexanecarboxylate
59. methyl trans,trans-4-(trans-4-hexylbicyclohexyl)cyclohexanecarboxylate
60. ethyl trans,trans-4-(trans-4-hexylbicyclohexyl)cyclohexanecarboxylate
61. propyl trans,trans-4-(trans-4-hexylbicyclohexyl)cyclohexanecarboxylate
62. butyl trans,trans-4-(trans-4-hexylbicyclohexyl)cyclohexanecarboxylate
63. pentyl trans,trans-4-(trans-4-hexylbicyclohexyl)cyclohexanecarboxylate
64. hexyl trans,trans-4-(trans-4-hexylbicyclohexyl)cyclohexanecarboxylate
65. heptyl trans,trans-4-(trans-4-hexylbicyclohexyl)cyclohexanecarboxylate
66. octyl trans,trans-4-(trans-4-hexylbicyclohexyl)cyclohexanecarboxylate
67. nonyl trans,trans-4-(trans-4-hexylbicyclohexyl)cyclohexanecarboxylate
68. decyl trans,trans-4-(trans-4-hexylbicyclohexyl)cyclohexanecarboxylate
69. methyl trans,trans-4-(trans-4-heptylbicyclohexyl)-cyclohexanecarboxylate
70. ethyl trans,trans-4-(trans-4-heptylbicyclohexyl)cyclohexanecarboxylate
71. propyl trans,trans-4-(trans-4-heptylbicyclohexyl)cyclohexanecarboxylate
72. butyl trans,trans-4-(trans-4-heptylbicyclohexyl)cyclohexanecarboxylate
73. pentyl trans,trans-4-(trans-4-heptylbicyclohexyl)cyclohexanecarboxylate
74. hexyl trans,trans-4-(trans-4-heptylbicyclohexyl)cyclohexanecarboxylate
75. heptyl trans,trans-4-(trans-4-heptylbicyclohexyl)cyclohexanecarboxylate
76. octyl trans,trans-4-(trans-4-heptylbicyclohexyl)cyclohexanecarboxylate
77. nonyl trans,trans-4-(trans-4-heptylbicyclohexyl)cyclohexanecarboxylate
78. decyl trans,trans-4-(trans-4-heptylbicyclohexyl)cyclohexanecarboxylate
79. methyl trans,trans-4-(trans-4-octylbicyclohexyl)cyclohexanecarboxylate
80. ethyl trans,trans-4-(trans-4-octylbicyclohexyl)cyclohexanecarboxylate
81. propyl trans,trans-4-(trans-4-octylbicyclohexyl)cyclohexanecarboxylate
82. butyl trans,trans-4-(trans-4-octylbicyclohexyl)cyclohexanecarboxylate
83. pentyl trans,trans-4-(trans-4-octylbicyclohexyl)cyclohexanecarboxylate
84. hexyl trans,trans-4-(trans-4-octylbicyclohexyl)cyclohexanecarboxylate
85. heptyl trans,trans-4-(trans-4-octylbicyclohexyl)cyclohexanecarboxylate
86. octyl trans,trans-4-(trans-4-octylbicyclohexyl)cyclohexanecarboxylate
87. nonyl trans,trans-4-(trans-4-octylbicyclohexyl)cyclohexanecarboxylate
88. decyl trans,trans-4-(trans-4-octylbicyclohexyl)cyclohexanecarboxylate
89. methyl trans,trans-4-(trans-4-nonylbicyclohexyl)cyclohexanecarboxylate
90. ethyl trans,trans-4-(trans-4-nonylbicyclohexyl)cyclohexanecarboxylate
91. propyl trans,trans-4-(trans-4-nonylbicyclohexyl)cyclohexanecarboxylate
92. butyl trans,trans-4-(trans-4-nonylbicyclohexyl)cyclohexanecarboxylate
93. pentyl trans,trans-4-(trans-4-nonylbicyclohexyl)cyclohexanecarboxylate
94. hexyl trans,trans-4-(trans-4-nonylbicyclohexyl)cyclohexanecarboxylate
95. heptyl trans,trans-4-(trans-4-nonylbicyclohexyl)cyclohexanecarboxylate
96. octyl trans,trans-4-(trans-4-nonylbicyclohexyl)cyclohexanecarboxylate
97. nonyl trans,trans-4-(trans-4-nonylbicyclohexyl)cyclohexanecarboxylate
98. decyl trans,trans-4-(trans-4-nonylbicyclohexyl)cyclohexanecarboxylate
99. methyl trans,trans-4-(trans-4-decylbicyclohexyl)cyclohexanecarboxylate
100. ethyl trans,trans-4-(trans-4-decylbicyclohexyl)cyclohexanecarboxylate
101. propyl trans,trans-4-(trans-4-decylbicyclohexyl)cyclohexanecarboxylate
102. butyl trans,trans-4-(trans-4-decylbicyclohexyl)cyclohexanecarboxylate
103. pentyl trans,trans-4-(trans-4-decylbicyclohexyl)cyclohexanecarboxylate
104. hexyl trans,trans-4-(trans-4-decylbicyclohexyl)cyclohexanecarboxylate
105. heptyl trans,trans-4-(trans-4-decylbicyclohexyl)cyclohexanecarboxylate
106. octyl trans,trans-4-(trans-4-decylbicyclohexyl)cyclohexanecarboxylate
107. nonyl trans,trans-4-(trans-4-decylbicyclohexyl)cyclohexanecarboxylate
108. decyl trans,trans-4-(trans-4-decylbicyclohexyl)cyclohexanecarboxylate.

EXAMPLES 109–189

Example 109

Trans,trans-4-(trans-4-propylbicyclohexyl)-1-pentanoylcyclohexane.

A solution of butyl magnesium bromide is prepared in a generally known manner from 0.6 g of Mg turnings, 10 ml of diethyl ether and 3.4 g of n-butyl bromide. A suspension of 6.5 g of trans,trans-4-(trans-4-propylbicyclohexyl)cyclohexane-1-carbonitrile in 20 ml of diethyl ether is added to this solution, with exclusion of atmospheric moisture. The mixture is boiled under reflux for 24 h and then initially 2 ml of ethanol are added cautiously, and then 30 ml of 10% hydrochloric acid are added. The organic phase is separated off, washed with water and dried with sodium sulfate. The residue remaining after the solvent has been evaporated off is recrystallised 2× from ethanol.

The following are prepared analogously:

110. trans,trans-4-(trans-4-propylbicyclohexyl)-1-acetylcyclohexane
111. trans,trans-4-(trans-4-propylbicyclohexyl)-1-propionylcyclohexane
112. trans,trans-4-(trans-4-propylbicyclohexyl)-1-butyrylcylohexane
113. trans,trans-4-(trans-4-propylbicyclohexyl)-1-hexanoylcyclohexane
114. trans,trans-4-(trans-4-propylbicyclohexyl)-1-heptanoylcyclohexane
115. trans,trans-4-(trans-4-propylbicyclohexyl-1-octanoylcyclohexane
116. trans,trans-4-(trans-4-propylbicyclohexyl)-1-nonanoylcyclohexane
117. trans,trans-4-(trans-4-propylbicyclohexyl)-1-decanoylcyclohexane
118. trans,trans-4-(trans-4-ethylbicyclohexyl)-1-acetylcyclohexane
119. trans,trans-4-(trans-4-ethylbicyclohexyl)-1-propionylcyclohexane
120. trans,trans-4-(trans-4-ethylbicyclohexyl)-1-butyrylcyclohexane
121. trans,trans-4-(trans-4-ethylbicyclohexyl)-1-pentanoylcyclohexane
122. trans,trans-4-(trans-4-ethylbicyclohexyl)-1-hexanoylcyclohexane
123. trans,trans-4-(trans-4-ethylbicyclohexyl)-1-heptanoylcyclohexane
124. trans,trans-4-(trans-4-ethylbicyclohexyl)-1-octanoylcyclohexane
125. trans,trans-4-(trans-4-ethylbicyclohexyl)-1-nonanoylcyclohexane
126. trans,trans-4-(trans-4-ethylbicyclohexyl)-1-decanoylcyclohexane
127. trans,trans-4-(trans-4-butylbicyclohexyl)-1-acetylcyclohexane
128. trans,trans-4-(trans-4-butylbicyclohexyl)-1-propionylcyclohexane
129. trans,trans-4-(trans-4-butylbicyclohexyl)-1-butyrylcyclohexane
130. trans,trans-4-(trans-4-butylbicyclohexyl)-1-pentanoylcyclohexane
131. trans,trans-4-(trans-4-butylbicyclohexyl)-1-hexanoylcyclohexane
132. trans,trans-4-(trans-4-butylbicyclohexyl)-1-heptanoylcyclohexane
133. trans,trans-4-(trans-4-butylbicyclohexyl)-1-octanoylcyclohexane
134. trans,trans-4-(trans-4-butylbicyclohexyl)-1-nonanoylcyclohexane
135. trans,trans-4-(trans-4-butylbicylohexyl)-1-decanoylcyclohexane
136. trans,trans-4-(trans-4-pentylbicyclohexyl)-1-acetylcyclohexane
137. trans,trans-4-(trans-4-pentylbicyclohexyl)-1-propionylcyclohexane
138. trans,trans-4-(trans-4-pentylbicyclohexyl)-1-butrylcyclohexane
139. trans,trans-4-(trans-4-pentylbicyclohexyl)-1-pentanoylcyclohexane
140. trans,trans-4-(trans-4-pentylbicyclohexyl)-1-hexanoylcyclohexane
141. trans,trans-4-(trans-4-pentylbicyclohexyl)-1-heptanoylcyclohexane
142. trans,trans-4-(trans-4-pentylbicyclohexyl)-1-octanoylcyclohexane
143. trans,trans-4-(trans-4-pentylbicyclohexyl)-1-nonanoylcyclohexane
144. trans,trans-4-trans-4-pentylbicyclohexyl)-1-decanoylcyclohexane
145. trans,trans-4-(trans-4-hexylbicyclohexyl)-1-acetylcyclohexane
146. trans,trans-4-(trans-4-hexylbicyclohexyl)-1-propionylcyclohexane
147. trans,trans-4-(trans-4-hexylbicyclohexyl)-1-butyrylcyclohexane
148. trans,trans-4-(trans-4-hexylbicyclohexyl)-1-pentanoylcyclohexane
149. trans,trans-4-(trans-4-hexylbicyclohexyl)-1-hexanoylcyclohexane
150. trans,trans-4-(trans-4-hexylbicyclohexyl)-1-heptanoylcyclohexane
151. trans,trans-4-(trans-4-hexylbicyclohexyl)-1-octanoylcyclohexane
152. trans,trans-4-(trans-4-hexylbicyclohexyl)-1-nonanoylcyclohexane
153. trans,trans-4-(trans-4-hexylbicyclohexyl)-1-decanoylcyclohexane
154. trans,trans-4-(trans-4-heptylbicyclohexyl)-1-acetylcyclohexane
155. trans,trans-4-(trans-4-heptylbicyclohexyl)-1-propionylcyclohexane
156. trans,trans-4-(trans-4-heptylbicyclohexyl)-1-butyrylcyclohexane
157. trans,trans-4-(trans-4-heptylbicyclohexyl)-1-pentanoylcyclohexane
158. trans,trans-4-(trans-4-heptylbicyclohexyl)-1-hexanoylcyclohexane
159. trans,trans-4-(trans-4-heptylbicyclohexyl)-1-heptanoylcyclohexane
160. trans,trans-4-(trans-4-heptylbicyclohexyl)-1-octanoylcyclohexane
161. trans,trans-4-(trans-4-heptylbicyclohexyl)-1-nonanoylcyclohexane
162. trans,trans-4-(trans-4-heptylbicyclohexyl)-1-decanoylcyclohexane
163. trans,trans-4-(trans-4-octylbicyclohexyl)-1-acetylcyclohexane
164. trans,trans-4-(trans-4-octylbicyclohexyl)-1-propionylcyclohexane
165. trans,trans-4-(trans-4-octylbicyclohexyl)-1-butyrylcyclohexane
166. trans,trans-4-(trans-4-octylbicyclohexyl)-1-pentanoylcyclohexane
167. trans,trans-4-(trans-4-octylbicyclohexyl)-1-hexanoylcyclohexane
168. trans,trans-4-(trans-4-octylbicyclohexyl)-1-heptanoylcyclohexane
169. trans,trans-4-(trans-4-octylbicyclohexyl)-1-octanoylcyclohexane
170. trans,trans-4-(trans-4-octylbicyclohexyl)-1-nonanoylcyclohexane
171. trans,trans-4-(trans-4-octylbicyclohexyl)-1-decanoylcyclohexane
172. trans,trans-4-(trans-4-nonylbicyclohexyl)-1-acetylcyclohexane 173. trans,trans-4-(trans-4-nonylbicyclohexyl)-1-propionylcyclohexane
174. trans,trans-4-(trans-4-nonylbicyclohexyl)-1-butyrylcyclohexane
175. trans,trans-4-(trans-4-nonylbicyclohexyl)-1-pentanoylcyclohexane
176. trans,trans-4-(trans-4-nonylbicyclohexyl)-1-hexanoylcyclohexane
177. trans,trans-4-(trans-4-nonylbicyclohexyl)-1-heptanoylcyclohexane
176. trans,trans-4-(trans-4-nonylbicyclohexyl)-1-octanoylcyclohexane
179. trans,trans-4-(trans-4-nonylbicyclohexyl)-1-nonanoylcyclohexane
180. trans,trans-4-(trans-4-nonylbicyclohexyl)-1-decanoylcyclohexane
181. trans,trans-4-(trans-4-decylbicyclohexyl)-1-acetylcyclohexane
182. trans,trans-4-(trans-4-decylbicyclohexyl)-1-propionylcyclohexane
183. trans,trans-4-(trans-4-decylbicyclohexyl)-1-butyrylcyclohexane
184. trans,trans-4-(trans-4-decylbicyclohexyl)-1-pentanoylcyclohexane
185. trans,trans-4-(trans-4-decylbicyclohexyl)-1-hexanoylcyclohexane
186. trans,trans-4-(trans-4-decylbicyclohexyl)-1-heptanoylcyclohexane
187. trans,trans-4-(trans-4-decylbicyclohexyl)-1-octanoylcyclohexane
188. trans,trans-4-(trans-4-decylbicyclohexyl)-1-nonanoylcyclohexane
189. trans,trans-4-(trans-4-decylbicyclohexyl)-1-decanoylcyclohexane

EXAMPLES 190–199

Example 190 trans,trans-4-(trans-4-propoxybicyclohexyl)-1-pentanoylcyclohexane.

A solution of butyl magnesium bromide is prepared from 0.2 g of Mg turnings, 5 ml of diethyl ether and 1.1 g of n-butyl bromide. A suspension of 2.2 g of trans,trans-4-(trans-4-propoxybicyclohexyl)cyclohexane-1-carbonitrile in 10 ml of diethyl ether is added to this solution, with exclusion of atmospheric moisture. The mixture is boiled under reflux for 24 h and then 2 ml of ethanol and 30 ml of 10% hydrochloric acid are added. The organic phase is washed with water and dried with sodium sulfate. The residue remaining after the solvent has been evaporated off is recrystallised twice from ethanol.

The following are prepared analogously:
191. trans,trans-4-(trans-4-methoxybicyclohexyl)-1-pentanoylcyclohexane
192. trans,trans-4-(trans-4-ethoxybicyclohexyl)-1-pentanoylcyclohexane
193. trans,trans-4-(trans-4-butoxybicyclohexyl)-1-pentanoylcyclohexane
194. trans,trans-4-(trans-4-pentoxybicyclohexyl)-1-pentanoylcyclohexane
195. trans,trans-4-(trans-4-hexoxybicyclohexyl)-1-pentanoylcyclohexane
196. trans,trans-4-(trans-4-heptoxybicyclohexyl)-1-pentanoylcyclohexane
197. trans,trans-4-(trans-4-octoxybicyclohexyl)-1-pentanoylcyclohexane
198. trans,trans-4-(trans-4-nonoxybicyclohexyl)-1-pentanoylcyclohexane
199. trans,trans-4-(trans-4-decoxybicyclohexyl)-1-pentanoylcyclohexane

EXAMPLE 200 trans,trans-4-(trans-4-propoxybicyclohexyl)-1-pentylcyclohexane 3 g of the ketone obtained in Example 190 are boiled under reflux for 2 h with 2 g of 85% hydrazine hydrate solution, 2.5 g of powdered KOH and 15 ml of triglycol. A mixture of hydrazine and water is then removed by distillation until the temperature in the reaction mixture is 195° C., and this temperature is maintained until the evolution of nitrogen has finished. After cooling, the mixture is diluted with the same volume of water and is extracted by shaking several times with dichloromethane. The combined organic phases are washed with water, dried with sodium sulfate and the solvent is removed by distillation. The residue is recrystallised twice from isopropanol.

The following are prepared analogously:

EXAMPLES 201 TO 262

201. trans,trans-4-(trans-4-propoxybicyclohexyl)-1-ethylcyclohexane
202. trans,trans-4-(trans-4-propoxybicyclohexyl)-1-propylcyclohexane
203. trans,trans-4-(trans-4-propoxybicyclohexyl)-1-butylcyclohexane
204. trans,trans-4-(trans-4-propoxybicyclohexyl)-1-hexylcyclohexane
205. trans,trans-4-(trans-4-propoxybicyclohexyl)-1-heptylcyclohexane
206. trans,trans-4-(trans-4-propoxybicyclohexyl)-1-octylcyclohexane
207. trans,trans-4-(trans-4-propoxybicyclohexyl)-1-nonylcyclohexane
208. trans,trans-4-(trans-4-propoxybicyclohexyl)-1-decylcyclohexane
209. trans,trans-4-(trans-4-ethoxybicyclohexyl)-1-ethylcyclohexane
210. trans,trans-4-(trans-4-ethoxybicyclohexyl)-1-propylcyclohexane
211. trans,trans-4-(trans-4-ethoxybicyclohexyl)-1-butylcyclohexane
212. trans,trans-4-(trans-4-ethoxybicyclohexyl)-1-hexylcyclohexane
213. trans,trans-4-(trans-4-ethoxybicyclohexyl)-1-heptylcyclohexane
214. trans,trans-4-(trans-4-ethoxybicyclohexyl)-1-octylcyclohexane
215. trans,trans-4-(trans-4-ethoxybicyclohexyl)-1-nonylcyclohexane
216. trans,trans-4-(trans-4-ethoxybicyclohexyl)-1-decylcyclohexane
217. trans,trans-4-(trans-4-ethoxybicyclohexyl)-1-pentylcyclohexane
218. trans,trans-4-(trans-4-butoxybicyclohexyl)-1-ethylcyclohexane
219. trans,trans-4-(trans-4-butoxybicyclohexyl)-1-propylcyclohexane
220. trans,trans-4-(trans-4-butoxybicyclohexyl)-1-butylcyclohexane
221. trans,trans-4-(trans-4-butoxybicyclohexyl)-1-hexylcyclohexane
222. trans,trans-4-(trans-4-butoxybicyclohexyl)-1-heptylcyclohexane 223. trans,trans-4-(trans-4-butoxybicyclohexyl)-1-octylcyclohexane
224. trans,trans-4-(trans-4-butoxybicyclohexyl)-1-nonylcyclohexane
225. trans,trans-4-(trans-4-butoxybicyclohexyl)-1-decylcyclohexane
226. trans,trans-4-(trans-4-butoxybicyclohexyl)-1-pentylcyclohexane
227. trans,trans-4-(trans-4-pentoxybicyclohexyl)-1-ethylcyclohexane
228. trans,trans-4-(trans-4-pentoxybicyclohexyl)-1-propylcyclohexane
229. trans,trans-4-(trans-4-pentoxybicyclohexyl)-1-butylcyclohexane
230. trans,trans-4-(trans-4-pentoxybicyclohexyl)-1-hexylcyclohexane
231. trans,trans-4-(trans-4-pentoxybicyclohexyl)-1-heptylcyclohexane
232. trans,trans-4-(trans-4-pentoxybicyclohexyl)-1-octylcyclohexane
233. trans,trans-4-(trans-4-pentoxybicyclohexyl)-1-nonylcyclohexane
234. trans,trans-4-(trans-4-pentoxybicyclohexyl)-1-decylcyclohexane
235. trans,trans-4-(trans-4-pentoxybicyclohexyl)-1-pentylcyclohexane
236. trans,trans-4-(trans-4-hexoxybicyclohexyl)-1-ethylcyclohexane
237. trans,trans-4-(trans-4-hexoxybicyclohexyl)-1-propylcyclohexane
238. trans,trans-4-(trans-4-hexoxybicyclohexyl)-1-butylcyclohexane
239. trans,trans-4-(trans-4-hexoxybicyclohexyl)-1-hexylcyclohexane
240. trans,trans-4-(trans-4-hexoxybicyclohexyl)-1-heptylcyclohexane
241. trans,trans-4-(trans-4-hexoxybicyclohexyl)-1-octylcyclohexane
242. trans,trans-4-(trans-4-hexoxybicyclohexyl)-1-nonylcyclohexane
243. trans,trans-4-(trans-4-hexoxybicyclohexyl)-1-decylcyclohexane
244. trans,trans-4-(trans-4-hexoxybicyclohexyl)-1-pentylcyclohexane
245. trans,trans-4-(trans-4-heptoxybicyclohexyl)-1-ethylcyclohexane
246. trans,trans-4-(trans-4-heptoxybicyclohexyl)-1-propylcyclohexane
247. trans,trans-4-(trans-4-heptoxybicyclohexyl)-1-butylcyclohexane
248. trans,trans-4-(trans-4-heptoxybicyclohexyl)-1-hexylcyclohexane
249. trans,trans-4-(trans-4-heptoxybicyclohexyl)-1-heptylcyclohexane
250. trans,trans-4-(trans-4-heptoxybicyclohexyl)-1-octylcyclohexane
251. trans,trans-4-(trans-4-heptoxybicyclohexyl)-1-nonylcyclohexane
252. trans,trans-4-(trans-4-heptoxybicyclohexyl)-1-decylcyclohexane
253. trans,trans-4-(trans-4-heptoxybicyclohexyl)-1-pentylcyclohexane
254. trans,trans-4-(trans-4-octoxybicyclohexyl)-1-ethylcyclohexane
255. trans,trans-4-(trans-4-octoxybicyclohexyl)-1-propylcyclohexane
256. trans,trans-4-(trans-4-octoxybicyclohexyl)-1-butylcyclohexane
257. trans,trans-4-(trans-4-octoxybicyclohexyl)-1-hexylcyclohexane
258. trans,trans-4-(trans-4-octoxybicyclohexyl)-1-heptylcyclohexane
259. trans,trans-4-(trans-4-octoxybicyclohexyl)-1-octylcyclohexane
260. trans,trans-4-(trans-4-octoxybicyclohexyl)-1-nonylcyclohexane
261. trans,trans-4-(trans-4-octoxybicyclohexyl)-1-decylcyclohexane
262. trans,trans-4-(trans-4-octoxybicyclohexyl)-1-pentylcyclohexane

EXAMPLE 263

2.0 g of butyryl chloride are added to a solution of 3.3 g of trans-4-(trans,trans-4-n-pentyl-4'-bicyclohexyl)-1-cyclohexanol (m.p. 232°) in 200 ml of pyridine, and the mixture is stirred overnight and then 700 ml of toluene are added. The toluene phase is washed successively with hydrochloric acid, NaOH solution and water, and is dried with $Na_2SO_4$. The residue remaining after the toluene has been evaporated off is recrystallised from acetone. Trans-4-(trans,trans-4-n-pentyl-4'-bicyclohexyl)-1-butyryloxycyclohexane is obtained.

EXAMPLES 264 TO 304

The following are prepared analogously:
264. trans-4-(trans,trans-4-pentyl-4'-bicyclohexyl)-1-acetoxycyclohexane.
265. trans-4-(trans,trans-4-pentyl-4'-bicyclohexyl)-1-propionyloxycyclohexane.
266. trans-4-(trans,trans-4-pentyl-4'-bicyclohexyl)-1-pentanoyloxycyclohexane.
267. trans-4-(trans,trans-4-pentyl-4'-bicyclohexyl)-1-hexanoyloxycyclohexane.
268. trans-4-(trans,trans-4-pentyl-4'-bicyclohexyl)-1-heptanoyloxycyclohexane.
269. trans-4-(trans,trans-4-pentyl-4'-bicyclohexyl)-1-octanoyloxycyclohexane.
270. trans-4-(trans,trans-4-ethyl-4'-bicyclohexyl)-1-acetoxycyclohexane.
271. trans-4-(trans,trans-4-ethy-4'-bicyclohexyl)-1-propionyloxycyclohexane.
272. trans-4-(trans,trans-4-ethyl-4'-bicyclohexyl)-1-butyryloxycyclohexane.
273. trans-4-(trans,trans-4-ethyl-4'-bicyclohexyl)-1-pentanoyloxycyclohexane.
274. trans-4-(trans,trans-4-ethyl-4'-bicyclohexyl)-1-hexanoyloxycyclohexane.
275. trans-4-(trans,trans-4-ethyl-4'-bicyclohexyl)-1-heptanoyloxycyclohexane.
276. trans-4-(trans,trans-4-ethyl-4'-bicyclohexyl)-1-octanoyloxycyclohexane.
277. trans-4-(trans,trans-4-propyl-4'-bicyclohexyl)-1-acetoxycyclohexane.
278. trans-4-(trans,trans-4-propyl-4'-bicyclohexyl)-1-propionyloxycyclohexane.
279. trans-4-(trans,trans-4-propyl-4'-bicyclohexyl)-1-butyryloxycyclohexane.
280. trans-4-(trans,trans-4-propyl-4'-bicyclohexyl)-1-pentanoyloxycyclohexane.
281. trans-4-(trans,trans-4-propyl-4'-bicyclohexyl)-1-hexanoyloxycyclohexane.
282. trans-4-(trans,trans-4-propyl-4'-bicyclohexyl)-1-heptanoyloxycyclohexane.
283. trans-4-(trans,trans-4-propyl-4'-bicyclohexyl)-1-octanoyloxycyclohexane.

284. trans-4-(trans,trans-4-butyl-4'-bicyclohexyl)-1-acetoxycyclohexane.
285. trans-4-(trans,trans-4-butyl-4'-bicyclohexyl)-1-propionyloxycyclohexane.
286. trans-4-(trans,trans-4-butyl-4'-bicyclohexyl)-1-butyryloxycyclohexane.
287. trans-4-(trans,trans-4-butyl-4'-bicyclohexyl)-1-pentanoyloxycyclohexane.
288. trans-4-(trans,trans-4-butyl-4'-bicyclohexyl)-1-hexanoyloxycyclohexane.
289. trans-4-(trans,trans-4-butyl-4'-bicyclohexyl)-1-heptanoyloxycyclohexane.
290. trans-4-(trans,trans-4-butyl-4'-bicyclohexyl)-1-octanoyloxycyclohexane.
291. trans-4-(trans,trans-4-hexyl-4'-bicyclohexyl)-1-acetoxycyclohexane.
292. trans-4-(trans,trans-4-hexyl-4'-bicyclohexyl)-1-propionyloxycyclohexane.
293. trans-4-(trans,trans-4-hexyl-4'-bicyclohexyl)-1-butyryloxycyclohexane.
294. trans-4-(trans,trans-4-hexyl-4'-bicyclohexyl)-1-pentanoyloxycyclohexane.
295. trans-4-(trans,trans-4-hexyl-4'-bicyclohexyl)-1-hexanoyloxycyclohexane.
296. trans-4-(trans,trans-4-hexyl-4'-bicyclohexyl)-1-heptanoyloxycyclohexane.
297. trans-4-(trans,trans-4-hexyl-4'-bicyclohexyl)-1-octanoyloxycyclohexane.
298. trans-4-(trans,trans-4-heptyl-4'-bicyclohexyl)-1-acetoxycyclohexane.
299. trans-4-(trans,trans-4-heptyl-4'-bicyclohexyl)-1-propionyloxycylohexane.
300. trans-4-(trans,trans-4-heptyl-4'-bicyclohexyl)-1-butyryloxycyclohexane.
301. trans-4-(trans,trans-4-heptyl-4'-bicyclohexyl)-1-pentanoyloxycyclohexane.
302. trans-4-(trans,trans-4-heptyl-4'-bicyclohexyl)-1-hexanoyloxycyclohexane.
303. trans-4-(trans,trans-4-heptyl-4'-bicyclohexyl)-1-heptanoyloxycyclohexane.
304. trans-4-(trans,trans-4-heptyl-4'-bicyclohexyl)-1-octanoyloxycyclohexane.

EXAMPLE 305

0.5 g of 35% KH dispersion is added to a solution of 1.1 g of trans-4-(trans,trans-4-n-pentyl-4'-bicyclohexyl)-1-cyclohexanol in 250 ml of THF, and the mixture is stirred under reflux for 2 hours. Then 0.6 g of n-iodobutane is added, and the mixture is stirred at room temperature for 2 hours. Excess potassium hydride is destroyed with water. The mixture is extracted with methylene chloride, and the solvent is dried with $Na_2SO_4$ and evaporated off. The residue which remains is worked up by chromatography (silica gel; ether/petroleum ether=1:25). Trans-4-(trans,trans-4-n-pentyl-4'-bicyclohexyl)-1-n-butoxycyclohexane is obtained.

The other homologous trans-4-(trans,trans-4-n-alkyl-4'-bicyclohexyl)-1-n-alkoxycyclohexanes are obtained from the appropriate hydroxyl compound and the appropriate n-alkyl halide in accordance with Example 305.

EXAMPLE 306

In analogy to Example 1, cis-4-[trans-4-(trans-4-n-propylcyclohexyl)cyclohexyl]cyclohexanecarbonitrile, m.p. 120°, c.p. 182°, is obtained from cis-4-[trans-4-(trans-4-n-propylcyclohexyl)cyclohexyl]cyclohexanecarboxylic acid (m.p. 206°, c.p. 270°).

The following are prepared analogously:
cis-4-[trans-4-(trans-4-ethylcyclohexyl)cyclohexyl]cyclohexanecarbonitrile
cis-4-[trans-4-(trans-4-butylcyclohexyl)cyclohexyl]cyclohexanecarbonitrile
cis-4-[trans-4-(trans-4-pentylcyclohexyl)cyclohexyl]cyclohexanecarbonitrile
cis-4-[trans-4-(trans-4-hexylcyclohexyl)cyclohexyl]cyclohexanecarbonitrile
cis-4-[trans-4-(trans-4-heptylcyclohexyl)cyclohexyl]cyclohexanecarbonitrile

EXAMPLE 307

In analogy to Example 2, methyl cis-4-[trans-4-(trans-4-n-propylcyclohexyl)cyclohexyl]cyclohexanecarboxylate, m.p. 119°, c.p. 131°, is obtained from cis-4-[trans-4-(trans-4-n-propylcyclohexyl)cyclohexyl]cyclohexanecarboxylic acid (m.p. 206°, c.p. 270°).

The following are prepared analogously:
ethyl cis-4-[trans-4-(trans-4-ethylcyclohexyl)cyclohexyl]cyclohexanecarboxylate
propyl cis-4-[trans-4-(trans-4-ethylcyclohexyl)cyclohexyl]cyclohexanecarboxylate
butyl cis-4-[trans-4-(trans-4-ethylcyclohexyl)cyclohexyl]cyclohexanecarboxylate
pentyl cis-4-[trans-4-(trans-4-ethylcyclohexyl)cyclohexyl]cyclohexanecarboxylate The following Examples relate to liquid-crystalline phases according to the invention.

EXAMPLE A

A mixture is prepared from (% by weight) 2% trans-4-(trans,trans-4-pentyl-4'-bicyclohexyl)-1-butyryloxycyclohexane
22% p-trans-4-propylcyclohexylbenzonitrile
36% p-trans-4-pentylcyclohexylbenzonitrile
25% p-trans-4-heptylcyclohexylbenzonitrile
15% 4'-(trans-4-pentylcyclohexyl)biphenyl-4-carbonitrile.
This mixture has a melting point of −4° C. and a clear point of 71° C.

EXAMPLE B

A mixture is prepared from (% by weight)
16% trans-4-(trans,trans-4-pentyl-4'-bicyclohexyl)-ethoxycyclohexane
12% trans-4-(trans,trans-4-pentyl-4'-bicyclohexyl)-1-butoxycyclohexane
17% p-trans-4-propylcyclohexylbenzonitrile
23% p-trans-4-pentylcyclohexylbenzonitrile
22% 4-ethyl-4'-(trans-4-pentylcyclohexyl)biphenyl and
10% 4-(trans-4-pentylcyclohexyl)-4'-(trans-4-propylcyclohexyl)biphenyl.

EXAMPLE C

A mixture of (% by weight)
26% trans,trans-4-ethylcyclohexylcyclohexane-4'-carbonitrile
17% trans,trans-4-propylcyclohexylcyclohexane-4'-carbonitrile
21% trans,trans-4-butylcyclohexylcyclohexane-4'-carbonitrile
26% trans,trans-4-heptylcyclohexylcyclohexane-4-carbonitrile
10% trans,trans-(trans-4-pentylbicyclohexyl)cyclohexane-1-carbonitrile
has a c.p. of 87° C.

EXAMPLE D

A mixture of (% by weight)

30% r-1-cyano-cis-4-(trans-4-pentylcyclohexyl)-1-pentylcyclohexane

27% r-1-cyano-cis-4-(trans-4-butylcyclohexyl)-1-heptylcyclohexane

28% r-1-cyano-cis-4-(trans-4-pentylcyclohexyl)-1-heptylcyclohexane

15% ethyl trans,trans-4-pentylbicyclohexyl)cyclohexanecarboxylate has a c.p. of 92° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a liquid crystalline phase having at least two liquid-crystalline components, the improvement wherein at least one component is a tercyclohexyl of the formula

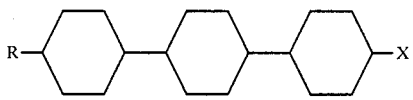

wherein
R is alkyl of 1-12C atoms,
X is —$COOR^1$, —$OOCR^1$, —$COR^1$ or $OR^2$; $R^2$ is alkyl of 1-11C atoms and
$R^1$ is alkyl of 1-12C atoms.

2. A phase of claim 1 wherein said compound is of the formula

R-Cyc-Cyc-Cyc-$OR^2$ or

R-Cyc-Cyc-Cyc-$OOCR^1$ wherein Cyc is 1,4-cyclohexylene.

3. A phase of claim 1 wherein in said compound all three 1,4-cyclohexylene groups are trans-substituted in the 1,4-positions.

4. A phase of claim 1 wherein in said compound all alkyl portions are straight chains.

5. A phase of claim 1 wherein in said compound all alkyl portions are of 2-10C atoms.

6. A phase of claim 1 wherein said compound is of the formula

Alkoxy-Cyc-Cyc-Cyc-alkyl

Alkyl-Cyc-Cyc-Cyc-COOAlkyl

Alkyl-Cyc-Cyc-Cyc-OOCAlkyl wherein Cyc is 1,4-cyclohexylene and the alkyl groups are of 1-10C atoms.

7. A compound of claim 1 wherein said phase is of the formula n-alkyl-Cyc-Cyc-Cyc-OOC-$CH_2CH_2CH_3$ n-alkyl-Cyc-Cyc-Cyc-O-$CH_2CH_3$ n-alkyl-Cyc-Cyc-Cyc-O-$CH_2CH_2CH_2CH_3$ wherein cyc is 1,4-cyclohexylene and the n-alkyl groups are of 2-8C atoms.

8. A phase of claim 1 wherein said compound is of formula

R-Cyc-Cyc-Cyc-$OR^2$

R-Cyc-Cyc-Cyc-$COOR^1$

R-Cyc-Cyc-Cyc-$OOCR^1$ wherein Cyc is 1,4-cyclohexylene.

9. In a liquid-crystal display element comprising a liquid crystal phase, the improvement wherein the phase is one of claim 1.

10. In an electrooptical display element comprising a liquid crystal dielectric, the improvement wherein the dielectric is a phase of claim 1.

* * * * *